United States Patent [19]

Thurow

[11] Patent Number: 4,637,834

[45] Date of Patent: Jan. 20, 1987

[54] AQUEOUS PROTEIN SOLUTIONS WHICH ARE STABLE TOWARDS DENATURING, PROCESSES FOR THEIR PREPARATION AND THEIR USE

[75] Inventor: Horst Thurow, Kelkheim, Fed. Rep. of Germany

[73] Assignee: Hoechst Aktiengesellschaft, Fed. Rep. of Germany

[21] Appl. No.: 825,965

[22] Filed: Feb. 5, 1986

Related U.S. Application Data

[63] Continuation of Ser. No. 629,847, Jul. 11, 1984, abandoned.

[30] Foreign Application Priority Data

Jul. 11, 1984 [DE] Fed. Rep. of Germany ....... 3325223

[51] Int. Cl.$^4$ ............................................. C08L 89/00
[52] U.S. Cl. ..................................... 106/124; 106/135; 106/146; 106/161; 514/773; 514/3
[58] Field of Search ............... 106/135, 161, 146, 124; 514/3, 773

[56] References Cited

U.S. PATENT DOCUMENTS 4,439,355 3/1984 Kenkare ............................ 106/125

FOREIGN PATENT DOCUMENTS 1146069 5/1983 Canada .
18609 11/1980 European Pat. Off. .

*Primary Examiner*—Theodore Morris
*Attorney, Agent, or Firm*—Finnegan, Henderson, Farabow, Garrett & Dunner

[57] ABSTRACT

The invention relates to aqueous solutions of proteins with a molecular weight above 8,500 daltons, which contain a compound of the formula I $$R^2O-X_n-R^3 \qquad (I)$$

in which $X_n$ is a chain of n members of the formula II or III

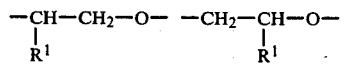

in any desired sequence, n denotes 2 to 200 and $R^1$ denotes hydrogen, methyl or ethyl, it being possible for the radicals $R^1$ to be identical or different but $R^1$ being hydrogen in at least half of the chain members, and $R^2$ and $R^3$ are identical or different and denote hydrogen or an organic radical, to processes for their preparation and to their use. The invention furthermore relates to the use of compounds of the formula I for the pretreatment of hydrophobic surfaces to avoid adsorption of denaturing of proteins.

9 Claims, No Drawings

AQUEOUS PROTEIN SOLUTIONS WHICH ARE STABLE TOWARDS DENATURING, PROCESSES FOR THEIR PREPARATION AND THEIR USE

This application is a continuation, of application Ser. No. 629,847, filed July 11, 1984, now abandoned.

The invention relates to aqueous solutions of proteins with a molecular weight above 8,500 daltons, the solutions being protected from adsorption at interfaces, against denaturing and against precipitation of the protein, and to processes for the preparation of such solutions. The invention furthermore relates to the use of such stabilized solutions for therapeutic purposes, preferably in metering units for the administration of medicaments.

It is known that dissolved proteins are adsorbed at hydrophobic interfaces (including the aqueous solution/air interface) (C. W. N. Cumper and A. E. Alexander, Trans. Faraday Soc. 46, 235 (1950)). Proteins are amphiphilic substances, i.e. they have both hydrophilic and hydrophobic regions. The hydrophobic regions form the contact to the hydrophobic interface.

As a result of the adsorption of the proteins at interfaces, various secondary reactions are observed. For example, "denaturing", i.e. a change in the shape of the adsorbed protein molecules (change in the tertiary and/or secondary structure) can occur. In addition, aggregation of adsorbed protein molecules may take place to give soluble or insoluble polymeric forms. Thus, many proteins are known to undergo surface aggregation, which manifests itself, for example, as turbidity of the solution or as biological inactivation of the proteins on stirring or shaking of the aqueous solutions (A. F. Henson, I. R. Mitchell, P. R. Musselwhite, J. Colloid Interface Sci. 32, 162 (1970)). This surface adsorption and aggregation is particularly adverse in apparatuses for the transportation of protein solutions, for example in automatic metering units for medicaments. In some cases, chemical reactions of the adsorbed proteins with dissolved substances also take place (F. MacRitchie, J. Macromol. Sci., Chem., 4, 1169 (1970)).

The interface processes described can furthermore impart to a protein immunogenic properties (i.e. the ability to induce immunological defence reactions in an organism) or they can intensify already existing immunogenic properties. In addition, biological properties, such as enzymatic, serological or hormonal activities, can be modified or destroyed.

A particular form of hydrophobic interfaces is formed when aqueous solutions are frozen, for example in the freeze-drying of proteins. The denaturing described for proteins can likewise take place at these interfaces (U. B. Hansson, Acta Chem. Scand., 22, 483 (1968)).

European Pat. No. A1-18,609 discloses aqueous protein solutions which contain, in order to avoid denaturing at interfaces of the proteins present therein, a surface-active substance with a chain-like basic structure, at least half of the chain members of which are methyl-substituted or ethyl-substituted oxyethylene units. The treatment of surfaces with such surface-active substances and their use for handling and cleaning proteins are also described.

No. WO-A1-83/00,288 furthermore discloses stable aqueous insulin formulations containing polyoxyethylene ($c_8$–$C_{15}$)-alkyl ethers for use in insulin-metering devices.

It has been found, surprisingly, that aqueous solutions of proteins with a molecular weight above 8,500 daltons can be stabilized particularly well by admixing substances characterized by the formula I:

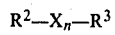
(I)

The invention thus relates to an aqueous solution of a protein with a molecular weight above 8,500 daltons, which contains a compound of the formula I

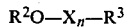
(I)

in which $X_n$ is a chain of n members of the formula II or III

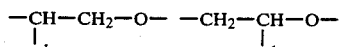

in any desired sequence, n denotes 2 to 200, preferably 4 to 100, and in particular 8 to 50, and $R^1$ denotes hydrogen, methyl or ethyl, it being possible for the radicals $R^1$ to be identical or different, but $R^1$ being hydrogen in at least half of the chain members, and $R^2$ and $R^3$ are identical or different and denote hydrogen or an organic radical. Preferred compounds of the formula I are those in which one of the radicals $R^2$ or $R^3$ represents hydrogen.

If $R^2$ or $R^3$ represent an organic radical, this is preferably understood as meaning an aliphatic radical with 1 to 20 carbon atoms, an alicyclic radical with 3 to 10 carbon atoms, an alicyclic-aliphatic radical with 4 to 20 carbon atoms, an aliphatic ester group with 2 to 20 carbon atoms, an aryl-aliphatic radical with 7 to 20 carbon atoms or an aryl radical with 6–20 carbon atoms, but in particular alkyl with 1 to 20 carbon atoms, alkanoyl with 2 to 20 carbon atoms or alkylphenyl with 1 to 10 alkyl-carbon atoms.

Examples of the radicals $R^2$ and $R^3$ are methyl, ethyl, propyl and butyl, and the radicals which are derived from lauryl alcohol or myristal alcohol; carboxalkyl groups which are derived from acetic acid, propionic acid, butyric acid, palmitic acid or stearic acid, and nonylphenoxy.

Compared with the additives known from European Pat. No. A1-18,609, stabilizing additives of this type have the advantage that, because of the longer polyoxyethylene chains ($R^1$=H) they have increased solubility in aqueous media. In addition, it has been found that when stabilizers of the type described are added, larger proteins in particular, i.e. those with a molecular weight of more than 8,500 daltons, can be protected from interface processes.

The protein solutions according to the invention can also contain a mixture of several different compounds of the formula I. Customary agents for adjusting the isotonicity, such as glycerol, sodium chloride, glucose or a similar carbohydrate, for preserving, such as phenol, cresol or methyl p-hydroxybenzoate, for buffering the pH value, such as sodium phosphate, acetate, citrate, barbital or tris-(hydroxymethyl)-aminomethane, and for achieving a depot action can furthermore be added to the solution.

The invention furthermore relates to a process for the preparation of these stable protein solutions, which comprises adding a surface-active substance of the formula I to an aqueous protein solution.

It is assumed that the surface-active substances according to the invention in the interface are of a shape such that the hydrophobic regions of the block polymers form the contact to the interface and that the hydrophilic polyoxyethylene regions project into the aqueous phase, so that they prevent direct interaction between the dissolved protein and the interface.

The relatively large hydrophilic polyoxyethylene regions of the stabilizers, which probably project into the aqueous phase, possibly cause only a coarse-meshed charge of the interface, so that smaller protein molecules cannot be prevented from adsorption at the interface.

Accordingly, the substances according to the invention are particularly suitable for stabilizing aqueous solutions of high molecular weight proteins. These proteins consist of one or more polypeptide chains and, besides amino acids, can also contain other units (sugars, lipids and the like).

The surface-active substances according to the invention are generally suitable for stabilizing those dissolved proteins which have a molecular weight above 8,500 daltons and which can adsorb at hydrophobic interfaces, such as, for example, polypeptides, globular proteins and compound proteins (proteids), in particular glycoproteins.

Examples which may be mentioned of such proteins are proteohormones, such as proinsulins and preproinsulins, enzymes, such as neuraminidase, galactosidase, glycosyl transferases, asparaginase, catalase and streptokinase, myoglobin and proteins with other functions, such as immunoglobulins of various classes and species, albumin, blood coagulation factors, interferons, interleucins and growth and differentiation factors. Proteins with a molecular weight above about 30,000 are preferred.

The invention furthermore relates to the use of the stable protein solutions defined above in the purification of proteins by crystallization, chromatography or ultrafiltration and their use for therapeutic purposes, in particular in metering apparatuses, such as implanted or external automatic pumps.

Hydrophobic surfaces which come into contact with protein solutions can advantageously be pretreated with the surface-active substances of the formula I in order to avoid adsorption or denaturing of the proteins.

The surface-active substances to be used according to the invention are prepared in a manner which is known per se by controlled addition of alkylene oxides onto alkylenediglycols (or onto corresponding hydroxy compounds). If appropriate, the terminal hydroxyl functions can then be esterified or etherified. General instructions on the preparation of a suitable block polymer are given in Example 1a.

EXAMPLE 1.

(a) 152.1 g of propylene glycol and 125 g of 49% strength potassium hydroxide solution are initially introduced into a 30 liter glass flask with a stirrer, heating bath and reflux condenser and a device for metering in alkylene oxides, under nitrogen. The mixture is dehydrated by vacuum distillation. 4,141 g of propylene oxide and 17,170 g of ethylene oxide are then slowly added successively at 120° C., with stirring. When the reaction has ended, the potassium hydroxide is neutralized by addition of lactic acid. The highly volatile constituents are removed and the product dehydrated by vacuum distillation. The average molecular weight of the product is 8,750 daltons, with a content of 80% by weight of polyoxyethylene in the molecule.

(b) 5 samples of in each case 7 ml of a 0.1% strength solution of egg albumin in 0.01 M phosphate buffer, pH 7, and 5 identical samples with the addition of a stabilizer of 0.1% (based on the weight of the solution) of a block polymer consisting of a linear chain of polypropylene glycol with an average molecular weight of 1,750 daltons, which was prepolymerized on both sides with in each case 40% of polyethylene glycol, were fused in 10 ml glass ampoules. The test solutions were mounted on a test tube rotator at a distance of 20 cm from the axletree and were rotated at 60 rpm in an incubation cabinet at 37° C. The samples with no stabilizer showed a marked turbidity after 5 days, caused by denatured protein. In contrast, the samples which contained the stabilizer were still clear after several months.

EXAMPLE 2

Samples of in each case 7 ml of a solution of 5% of human immunoglobulins, a solution of 0.5% of myoglobin (horse) and a solution of 0.1% of β-galactosidase and identical samples with an addition of 0.1% (based on the weight of the solution) of a block polymer consisting of a linear chain of polypropylene glycol with an average molecular weight of 1,750 daltons, which was prepolymerised on both sides with in each case 50% of polyethylene glycol, were fused in 10 ml glass ampoules.

The samples were shaken at 37° C. as described in Example 1b. The samples with no stabilizer were turbid after a few days, and in the case of the β-galactosidase the enzymatic activity had fallen to less than 3% of the initial value. In contrast, the samples which contained the stabilizer were still clear even after several weeks. Virtually the full enzymatic activity was retained.

EXAMPLE 3

A solution containing 1% of human immunoglobulins in 0.01 M phosphate buffer, pH 7, and, for stabilization, tion, 0.2% (based on the weight of the solution) of a block polymer consisting of a linear chain of polypropylene glycol with an average molecular weight of 1,750 daltons, which was prepolymerized on both sides with 40% of polyethylene glycol, was prepared.

The solution was introduced into an automatically controlled metering apparatus. On an agitation simulator in an incubating cabinet at 37° C., the metering apparatus delivered a clear solution for several weeks. The immunoglobulin contents were measured in the clear solution delivered. They agreed with the initial values.

The experiment was repeated with a 1% strength immunoglobulin solution which contained no stabilizer. In this case, precipitates were formed in the delivery tubes of the metering apparatus after a few days. The clear supernatant liquor contained virtually no more immunoglobulins.

EXAMPLE 4

5 samples of in each case 7 ml of a solution of 350,000 units of human fibroblast interferon in phosphate buffer, pH 7, and 5 analagous samples which additionally contained 0.01% (based on the weight of the solution) of the following compound $$CH_3(CH_2)_{12}-CH_2-O(-CH_2-CH_2-O)_{12}(-CH_2-\overset{\overset{\displaystyle CH_3}{|}}{CH}-O)_7H$$

were fused in 10 ml glass ampoules. The test solutions were rotated at 37° C. as described in Example 1b. In the 5 non-stabilized samples, a loss in biological activity of more than 95% was measured after 2 days. The biological activity of the interferon in the 5 samples which contained the stabilizer was unchanged even after several weeks.

I claim:

1. An aqueous solution of a protein with a molecular weight above 8,500 daltons, which contains a compound of the formula I $$R^2O-X_n-R^3 \qquad (I)$$

in which $X_n$ is a chain of n members of the formula II or III $$\underset{(II)}{-CH-CH_2-O-} \quad \underset{(III)}{-CH_2-CH-O-}$$
$$\underset{}{\overset{|}{R^1}} \qquad \underset{}{\overset{|}{R^1}}$$

in any desired sequence, n denotes 2 to 200, preferably 4 to 100 and $R^1$ denotes hydrogen, methyl or ethyl, it being possible for the radicals $R^1$ to be identical or different, but $R^1$ being hydrogen in more than 75% of the chain members, and $R^2$ and $R^3$ are identical or different and denote hydrogen or an organic radical, such that the protein is protected from adsorption at interfaces and protected against denaturing and precipitation.

2. A aqueous protein solution as claimed in claim 1, in which $R^2$ and $R^3$ independently of one another denote hydrogen, an aliphatic radical with 1 to 20 carbon atoms, an alicyclic radical with 3 to 10 carbon atoms, an alicyclic-aliphatic radical with 4 to 20 carbon atoms, an aliphatic ester group with 2 to 20 carbon atoms, an arylaliphatic radical with 7 to 20 carbons atoms or an aryl radical with 6 to 20 carbon atoms.

3. An aqueous protein solution as claimed in claim 1, in which $R^2$ and $R^3$ independently of one another denote hydrogen, alkyl with 1 to 20 carbon atoms, alkanoyl with 2 to 20 carbon atoms or alkylphenyl with 1 to 10 alkylcarbon atoms.

4. An aqueous protein solution as claimed in claim 1, which contains a mixture of at least two different compounds of the formula I.

5. An aqueous protein solution as claimed in claim 1, which contains customary additives for adjusting the isotonicity, for preservation, for buffering and/or for achieving a depot action.

6. An aqueous protein solution as claimed in claim 1, which contains at least two different proteins.

7. An aqueous solution as claimed in claim 1 where the concentration of the compound of formula I is between 0.01% and 0.2% (based on the weight of the solution).

8. A medicament suitable for administration by metering units comprising an aqueous solution of a protein with a molecular weight above 8,500 daltons, which contains a compound of the formula I $$R^2O-X_n-R^3 \qquad (I)$$

in which $X_n$ is a chain of n members of the formula II or III $$\underset{(II)}{-CH-CH_2-O-} \quad \underset{(III)}{-CH_2-CH-O-}$$
$$\underset{}{\overset{|}{R^1}} \qquad \underset{}{\overset{|}{R^1}}$$

in any desired sequence, n denotes 2 to 200, preferably 4 to 100, and $R^1$ denotes hydrogen, methyl or ethyl, it being possible for the radicals $R^1$ to be identical or different, but $R^1$ being hydrogen in more than half of the chain members, and $R^2$ and $R^3$ are identical or different and denote hydrogen or an organic radical.

* * * * *